United States Patent [19]

Kleiner

[11] Patent Number: 5,432,291
[45] Date of Patent: Jul. 11, 1995

[54] PREPARATION OF ACYLAMINOMETHANEPHOSPHONIC ACIDS AND ACYLAMINOMETHANEPHOSPHINIC ACIDS

[75] Inventor: Hans-Jerg Kleiner, Kronberg/Taunus, Germany

[73] Assignee: Hoechst Aktiengesellschaft, Frankfurt am Main, Germany

[21] Appl. No.: 969,167

[22] PCT Filed: Aug. 7, 1991

[86] PCT No.: PCT/EP91/01495
§ 371 Date: Feb. 11, 1993
§ 102(e) Date: Feb. 11, 1993

[87] PCT Pub. No.: WO92/03450
PCT Pub. Date: Mar. 5, 1992

[30] Foreign Application Priority Data

Aug. 17, 1990 [DE] Germany .................. 40 26 026.7

[51] Int. Cl.$^6$ ............................................. C07C 1/00
[52] U.S. Cl. ..................................................... 562/15
[58] Field of Search .......................................... 562/15

[56] References Cited

FOREIGN PATENT DOCUMENTS 0370992  5/1990  European Pat. Off. .
3824961  1/1990  Germany .

OTHER PUBLICATIONS

German Abstract 3824-961-A. (1-25-90).
Chemical Abstract vol. 107, 1987, 39933j, p. 714.
Synthesis, 1989, pp. 547–548.
Liebigs Ann. Chem. 1988, pp. 861–867.

Primary Examiner—José G. Dees
Assistant Examiner—Joseph M. Conrad, III
Attorney, Agent, or Firm—Curtis, Morris & Safford

[57] ABSTRACT

Acylaminomethanephosphinic acids, and a process for the preparation of acylaminomethanephosphonic acids and acylaminomethylphosphinic acids Acylaminomethanephosphonic acid and acylaminomethylphosphinic acids of the formula I, $$R^2-CO-NH-CH_2-P(O)(OH)R^1 \qquad (I)$$

in which $R^1$ is hydroxyl, $C_1$-$C_4$-alkyl or phenyl and $R^2$ is H, $C_1$-$C_6$-alkyl, benzyl or phenyl, unsubstituted or substituted by one or more radicals from the group comprising $C_1$-$C_4$-alkyl, $C_1$-$C_4$-alkoxy and halogen, are valuable intermediates for the preparation of biologically active compounds.

They can be prepared by reacting a compound of the formula II $$R^2-CO-NH-CH_2-OH \qquad (II)$$

with compounds of the formula III, $$H-P(O)(OH)R^1 \qquad (III)$$

in the presence of an at least equimolar amount of acetic anhydride, based on the compound of the formula II.

The compounds of the formula (I) where $R^1$ is other than hydroxyl, are novel.

17 Claims, No Drawings

PREPARATION OF ACYLAMINOMETHANEPHOSPHONIC ACIDS AND ACYLAMINOMETHANEPHOSPHINIC ACIDS

DESCRIPTION

Acylaminomethylphosphinic acids, and a process for the preparation of acylaminomethanephosphonic acids and acylaminomethylphosphinic acids Acylaminomethanephosphinic acids, and a process for the preparation of acylaminomethanephosphonic acids and acylaminomethanephosphinic acids acylaminomethanephosphonic acids are valuable intermediates for the preparation of aminomethanephosphonic acid, which is of industrial interest. They are also particularly suitable as intermediates for the preparation of the herbicidally active N-phosphonomethylglycine by reaction with glyoxylic acid (see U.S. Pat. No. 4,851,159). To date, the acylaminomethanephosphonic acids can be obtained, for example, by reacting N-hydroxymethylamides with phosphorus trichloride followed by hydrolysis with hydrochloric acid (U.S. Pat. No. 2,304,156; U.S. Pat. No. 2,328,358). A particular disadvantage of this process consists in the formation of bischloromethyl ether as an undesirable by-product, which has been identified as a carcinogenic working substance. Bischloromethyl ether is formed by reacting formaldehyde and hydrochloric acid in a hydrolysis step, traces of formaldehyde being contained in the N-hydroxymethylamides, for production reasons. The removal of all traces of bischloromethyl ether requires complicated purification steps. The object is therefore to provide a process which excludes the formation of bischloromethyl ether and which can be applied on an industrial scale.

The invention relates to a process for the preparation of compounds of the formula I

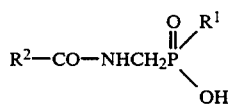
(I)

in which $R^1$ is hydroxyl, $C_1$–$C_4$-alkyl or phenyl and $R^2$ is H, $C_1$–$C_6$-alkyl, preferably $C_1$–$C_3$-alkyl, benzyl or phenyl, unsubstituted or substituted by one or more radicals from the group comprising $C_1$–$C_4$-alkyl, $C_1$–$C_4$-alkoxy and halogen, which comprises reacting compounds of the formula II

in which $R^2$ has the abovementioned meaning, with compounds of the formula III,

(III)

in which $R^1$ has the abovementioned meaning, in the presence of an at least equimolar amount of acetic anhydride, based on the compound of the formula II.

The invention furthermore relates to acylaminomethylphosphinic acids of the formula I mentioned, in which $R^1$ and $R^2$ are as defined above, with the exception of compounds in which $R^1$ is hydroxyl. The compounds are valuable intermediates for the preparation of aminomethylphosphinic acids which have biological activity (S. L. Maier in "Advances in the Chemistry of Aminophosphonic Acids" in "Phosphorus and Sulfur" 14, 195–322 (1983) and the references cited therein). Preferred acylaminomethylphosphinic acids of the formula I are those in which $R^1$ and $R^2$ have the preferred meanings given above.

Examples of suitable starting compounds for the process according to the invention are: N-hydroxymethylformamide, N-hydroxymethylacetamide and, in particular, N-hydroxymethylbenzamide. Examples of acids of the formula III are phosphorous acid, methanephosphonous acid and benzenephosphonous acid. The compounds of the formulae II and III are generally known and commercially available or readily accessible by known processes.

The molar ratio of the components is an important factor which determines the yield. The starting substances N-hydroxymethylamide of the formula II, acid of the formula III and acetic anhydride are preferably employed in a molar ratio of 1:1:1.5 to 1:(1–1.1):8, in particular in a molar ratio of 1:1:1.5 to 1:1:4. A further excess of acetic anhydride is possible.

If appropriate, the reaction of II and III can be carried out in an organic solvent.

Examples of suitable solvents are polar protic and aprotic organic solvents such as acetic acid, acetonitrile, tetrahydrofuran or dioxane. Acetic acid is the preferred solvent. The use of solvents can also be dispensed with.

For example, the process is expediently carried out in such a way that the reactants of the formulae II and III and acetic anhydride are mixed in a temperature range of 5° to 60° C., if appropriate with cooling. In this context, the sequence in which the components are added is not critical. For example, the solution of the acid of the formula III in the organic solvent such as acetic acid can be metered into the acetic anhydride, and the N-hydroxymethylamide of the formula II, which is optionally dissolved in a solvent, can be added batchwise or continuously to this mixture. After mixing, stirring is continued, if appropriate, for example in a temperature range of 10° to 60° C., and the mixture is then preferably refluxed. When the reaction is complete, it may make sense to hydrolyze the amount of excess acetic anhydride contained in the reaction mixture, first by adding water, followed by further heating. Then, the organic solvent which may have been added in the previous reactions is preferably removed, for example by distillation, if appropriate under reduced pressure. Alternatively, the reaction material in crystallized form can be separated for example from the organic solvent by filtration with suction.

The process is preferably carried out in such a way that acetic anhydride and the reactants of the formulae II and III are mixed at temperatures from 5° to 60° C., if appropriate with cooling, and the mixture is then refluxed until the reaction is complete.

Working-up can be carried out by generally customary methods. For example, it is possible to first remove lower-boiling substances by distillation in vacuo. The residues which are obtained can then be digested with water or other solvents such as, for example, acetone, acetonitrile, acetic acid, methanol, ethanol or isopropanol, if appropriate with heating. The crystalline product which is obtained is then separated off and can be purified further by customary methods. Moreover, it can be advantageous to hydrolyze the amount of excess acetic anhydride which is contained in the reaction mixture prior to further working-up. If N-hydroxymethylbenzamide is used, some of the end products are then obtained in crystalline form as soon as the mixture is cooled.

The crude products can be purified further in a simple manner by crystallization. It is a peculiarity of the process that the end products obtained, of the formula (I), when $R^2$ is not methyl, can contain amounts of compounds of the formula (I) in which $R^2$ is methyl as a by-product. These amounts of by-product are as valuable as the main components of the process according to the invention for further processing the end products in accordance with the process of U.S. Pat. No. 4,851,159. If desired, the by-products can be separated off by customary separation processes.

EXAMPLE 1

302 g (2.0 mol) of N-hydroxymethylbenzamide were placed in 200 ml of acetic acid and the mixture was cooled to 10° C. A solution of 164 g (2.0 mol) of phosphorous acid in 200 ml of acetic acid was then added dropwise at the same temperature in the course of 15 minutes, with stirring and cooling. Towards the end of the dropwise addition, an almost clear solution was formed. Then, 521 g (5.11 mol) of acetic anhydride were rapidly added dropwise, during which process the temperature did not rise above 53° C., with cooling. The mixture was then kept under reflux for 2.5 hours. After the mixture had been cooled to room temperature, 56 g (3.1 mol) of water were added, with cooling. The mixture was subsequently kept under reflux for 30 minutes. Approximately 110 ml of acetic acid were subsequently distilled off under reduced pressure, and the reaction solution which remained was stirred overnight and solids were subsequently filtered off with suction. 340 g (approx. 80% of theory) of a crystalline mixture of approx. 70% of benzoylaminomethanephosphonic acid, approx. 20% of acetylaminomethanephosphonic acid and further phosphonic acids (according to $^{31}$P-NMR spectrum) were obtained. The mixture had a melting point of 156° to 163° C. After recrystallisation from water, pure benzoylaminomethanephosphonic acid of a melting point of 176°–177° C. was obtained.

EXAMPLE 2

561 g (5.5 mol) of acetic anhydride were cooled to 10° C. Then, a solution of 164 g (2.0 mol) of phosphorous acid and 300 ml of acetic acid were added dropwise in the course of one hour, with stirring and cooling. 302 g (2.0 mol) of N-hydroxymethylbenzamide were then added in portions in the course of 50 minutes at 10°–15° C., with cooling. Stirring was continued at 10° C. for 20 minutes. The reaction mixture was subsequently kept under reflux for 2.5 hours, followed by cooling. 61 g (3.39 mol) of water were then added dropwise at 25°–30° C., with cooling and stirring. After this, the mixture was refluxed again. After cooling, the mixture was stirred overnight and solids were then filtered off with suction. 320 g (approx. 75% of theory) of crude benzoylaminomethanephosphonic acid were obtained. Further crude acid could be obtained from the mother liquor.

EXAMPLE 3

43.3 g (0.424 mol) of acetic anhydride were cooled to 10° C. A solution of 16 g (0.2 mol) of methane phosphonous acid in 40 ml of acetic acid was then added dropwise, with stirring and cooling. 30.2 g (0.2 mol) of N-hydroxymethylbenzamide were subsequently added in portions in the course of 10 minutes, with cooling. The cooling was then removed, during which process the internal temperature rose to 32° C. The mixture was then refluxed for 2.5 hours and, after this, cooled. The mixture was subsequently concentrated under reduced pressure to an internal temperature of 95° C. 46.7 g of crude product remained as the residue which was dissolved in hot water and filtered off with suction while hot. The filtrate was reconcentrated under reduced pressure to 95° C. 38.3 g of a crystalline residue were obtained. After recrystallisation from water, 24 g (56% of theory) of (benzoylaminomethyl)(methyl)phosphinic acid of a melting point of 144° to 146° C. were obtained; the CHNP analysis of the sample revealed:

$C_9H_{12}NO_3$ P calc.: 50.70% C 5.67% H 6.57% N 14.53% P (213) found: 51.2% C 5.8% H 6.5% N 14.2% P

EXAMPLE 4

43.2 g (0.424 mol) of acetic anhydride were cooled to 10° C. A solution of 28.2 g (0.2 mol) of benzenephosphonous acid in 40 ml acetic acid were then added dropwise at 15° C., with stirring and cooling. After this, 30.2 g (0.2 mol) of N-hydroxymethylbenzamide were added in portions in the course of 10 minutes at 15° C., with cooling. After this, the cooling was removed, during which process the internal temperature rose to 35° C. After this, the mixture was refluxed for 3 hours and subsequently cooled. 175 ml of water were then added; during this process, the temperature rose to 35° C. The mixture was refluxed again, and finally cooled again, with stirring. After crystallisation, a total of 40 g (73% of theory) of benzoylaminomethylphenylphosphinic acid of a melting point of 158°–160° C. were obtained. CHNP analysis revealed:

$C_{14}H_{14}NO_3P$ calc.: 61.09% C 5.13% H 5.09% N 11.25% P (275) found: 61.2 % C 5.2% H 5.3% N 10.7% P

EXAMPLE 5

40.8 g (0.4 mol) of acetic anhydride were cooled to 10° C. After this, 16.4 g (0.2 mol) of phosphorous acid were introduced in the course of 5 minutes, with stirring and cooling. 17.8 g (0.2 mol) of N-hydroxymethylacetamide were subsequently added dropwise at 10° C. in the course of 10 minutes. After this, the mixture was first allowed to come to room temperature and then refluxed for 2.5 hours. The mixture was subsequently cooled. 10 ml of water were then added in portions. After this, the mixture was kept under reflux for 1 hour. After this, a mixture of 10 ml of acetic acid and 1.5 ml of water was added, and stirring was continued. After crystallisation and filtration with suction, 16.3 g (53% of theory) of acetylaminomethanephosphonic acid of a melting point of 188°–194° C. were obtained.

I claim:

1. A process for the preparation of compounds of the formula (I)

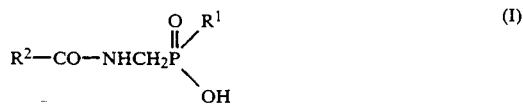

in which $R^1$ is hydroxyl, $C_1$-$C_4$-alkyl or phenyl and $R^2$ is H, $C_1$-$C_6$-alkyl, benzyl or phenyl, unsubstituted or substituted by one or more radicals from the group comprising $C_1$-$C_4$-alkyl, $C_1$-$C_4$-alkoxy and halogen, which comprises reacting compounds of the formula II $$R^2-CO-NH-CH_2-OH \qquad (II)$$

in which $R^2$ has the abovementioned meaning, with compounds of the formula III,

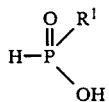
(III)

in which $R^1$ has the abovementioned meaning, in the presence of an at least equimolar amount of acetic anhydride, based on the compound of the formula II.

2. The process as claimed in claim 1, wherein $R^1$ is hydroxyl.

3. The process as claimed in claim 2, wherein $R^2$ is phenyl.

4. The process as claimed in claim 1, wherein $R^1$ is methyl, ethyl or phenyl.

5. The process as claimed in claim 4, wherein $R^2$ is phenyl.

6. The process as claimed in claim 1, wherein $R^2$ is H, $C_1$-$C_3$-alkyl, benzyl or phenyl.

7. The process as claimed in claim 1, 2 or 4, wherein $R^2$ is phenyl.

8. The process as claimed claim 1 wherein the compounds of the formulae II and III and acetic anhydride are reacted in a molar ratio of 1:1:1.5 to 1:(1-1.1):8.

9. The process as claimed in claim 8, wherein the molar ratio is 1:1:1.5 to 1:1:4.

10. The process as claimed in claim 8, wherein excess acetic anhydride is hydrolysed when the reaction is complete.

11. The process as claimed in claim 1 wherein the reaction of the compounds of the formulae II and III is carried out in the presence of an organic solvent.

12. The process as claimed in claim 11, wherein the solvent is acetic acid.

13. A process for the preparation of compounds of the formula (I)

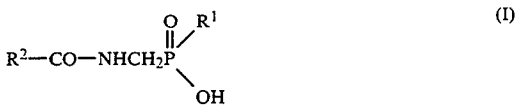
(I)

in which $R^1$ is hydroxyl, methyl, ethyl or phenyl, which comprises reacting compounds of the formula (II)

$$R^2-CO-NH-CH_2-OH \qquad (II)$$

in which $R^2$ is H, $C_1$-$C_3$-alkyl, benzyl or phenyl, with compounds of formula III,

(III)

in which $R^1$ has the above-mentioned meaning, in the presence of an at least equimolar amount of acetic anhydride, based on the compound of formula II.

14. The process as claimed in claim 13, wherein the molar compounds of the formulae (II) and (III) and acetic anhydride are reacted in a molar ratio of 1:1:1.5 to 1:(1-1.1):8.

15. The process as claimed in claim 14, wherein excess acetic anhydride is hydrolysed when the reaction is complete.

16. The process as claimed in claim 14, wherein $R^2$ is phenyl.

17. The process as claimed in claim 13, wherein the reaction of the compounds of the formulae (II) and (III) is carried out in the presence of an organic solvent.

* * * * *